(12) United States Patent
Wilson et al.

(10) Patent No.: US 10,330,686 B2
(45) Date of Patent: Jun. 25, 2019

(54) ASSAY FOR ANTI-POLYVINYL ALCOHOL ANTIBODIES

(71) Applicant: AUTOIMMUNE TECHNOLOGIES, LLC, New Orleans, LA (US)

(72) Inventors: Russell B. Wilson, Mandeville, LA (US); Kevin David Simpson, New Orleans, LA (US)

(73) Assignee: Autoimmune Technologies, LLC, New Orleans, LA (US)

( * ) Notice: Subject to any disclaimer, the term of this patent is extended or adjusted under 35 U.S.C. 154(b) by 109 days.

(21) Appl. No.: 15/299,318

(22) Filed: Oct. 20, 2016

(65) Prior Publication Data
US 2018/0113124 A1    Apr. 26, 2018

(51) Int. Cl.
*G01N 33/543* (2006.01)
*G01N 33/53* (2006.01)
*G01N 33/545* (2006.01)
*G01N 33/68* (2006.01)
G01N 33/548 (2006.01)
G01N 33/553 (2006.01)

(52) U.S. Cl.
CPC ..... *G01N 33/6854* (2013.01); *G01N 2430/60* (2013.01); *G01N 2650/00* (2013.01)

(58) Field of Classification Search
None
See application file for complete search history.

(56) References Cited

U.S. PATENT DOCUMENTS 5,834,215 A    11/1998  Garry et al.
6,214,566 B1    4/2001  Asa et al.

OTHER PUBLICATIONS

Anton et al. Opinion of the scientific panel on food additives, flavourings, processing aids and materials in contact with food on a request from the commission related to the use of polyvinyl alcohol as a coating agent for food supplements. The EFSA Journal, 2005, vol. 294, pp. 1-15. (Year: 2005).*

Bazzichi, L. et al., Antipolymer Antibody in Italian Fibromyalgic Patients, Arthritis Research & Therapy 9, R86, 1-5, (2007).
David, A. et al., Gulf War Illness: New American Research Provides Leads But No Firm Conclusions, The BMJ 314: 239, 1-4 (1997).
De Jong, W.H. et al., Study to Determine the Presence of Antipolymer Antibodies in a Group of Dutch Women With a Silicone Breast Implant, Clinical and Experimental Rheumatology 20: 151-160 (2002).
Edlavitch, L., The Lancet, vol. 349, 1170 (1997).
Fukuda, K. et al., Chronic Multisymptom Illness Affecting Air Force Veterans of the Gulf War, Journal American Medical Association (JAMA) vol. 280 (11), 981-988 (1998).
Grady, E.P. et al., Rheumatic Findings in Gulf War Veterans, Arch Intern Medicine vol. 158, 367-371 (1998).
Haley, R.W. et al., Self-Reported Exposure to Neurotoxic Chemical Combinations in the Gulf War: A Cross-Sectional Epidemiologic Study, Journal American Medical Association vol. 277 (3), 231-237 (1997).
Hyams, K.C. et al., War Syndromes and Their Evaluation: From the U.S. Civil War to the Persian Gulf War, Annals of Internal Medicine 125 (5), 398-405 (1996).
Kleinau, S. et al., Role of Adjuvants in Turning Autoimmunity Into Autoimmune Disease, Scandinavian Journal of Rheumatology 24: Suppl.101, 179-181 (1995).
Lorentzen, J.C. et al., Susceptibility of DA Rats to Arthritis Induced With Adjuvant Oil or Rat Collagen is Determined by Genes Both Within and Outside the Major Histocompatibility Complex, Scandinavian Journal of Immunology 44, 592-598 (1996).
Madzhidov, U.V. et al., Genetic Control of Sensitivity to Experimental Adjuvant Arthritis in Inbred Mice, Research Laboratory of Experimental Biological Models, (translated from Byulleten Eksperimental noi Biologii i Meditsiny) vol. 102 (7), 74-76 (1986).
Persian Gulf Veterans Coordinating Board, Unexplained Illnesses Among Desert Storm Veterans, A Search for Causes, Treatment and Cooperation, Arch Intern Medicine 155, 262-268 (1995).

* cited by examiner

*Primary Examiner* — Shafiqul Haq
(74) *Attorney, Agent, or Firm* — Olson & Cepuritis, Ltd.

(57) ABSTRACT

An assay method for detecting antipolyvinyl alcohol (anti-PVAL) antibodies in test samples, such as serum, is described. The method comprises combining a sample to be tested for an anti-PVAL antibody with polyvinyl alcohol (PVAL) to form a binary complex of the PVAL with an anti-PVAL antibody in the sample, followed by reacting an indicator reagent with the binary complex to form a labeled ternary complex, and then detecting the presence or absence of the ternary complex in the sample. Kits for performing the test are also described.

11 Claims, 7 Drawing Sheets

ASSAY FOR ANTI-POLYVINYL ALCOHOL ANTIBODIES

FIELD OF THE INVENTION

The invention relates to methods and immunoassay kits that are useful for detection of anti-polyvinyl alcohol antibodies.

BACKGROUND OF THE INVENTION

There are a number of illnesses and conditions with unknown etiology, such as atypical connective tissue diseases (e.g., fibromyalgia, chronic fatigue syndrome, and the symptoms associated with exposure to silicone breast implants), and Gulf War Syndrome (GWS), which currently are the focus of considerable research to determine causative agents and treatments. GWS is a blanket term for the illnesses afflicting men and women who served in the Persian Gulf military conflict during 1990-1991 remain ill-defined. GWS is characterized by a variety of symptoms including fatigue, rashes, headaches, arthralgias, myalgias, diarrhea, memory loss, autoimmune thyroid disease, increased allergies and sensitivities to environmental elements, and neurological abnormalities (Grady, et al. *Arch. Int. Med.,* 1998, 158: 367-371; Persian Gulf Veterans Coordinating Board. *Arch. Int. Med.,* 1995, 155: 262-268; Haley, et al. *J.A.M.A.,* 1997, 277: 231-237). While GWS patients do not in general suffer from classic rheumatic diseases, the signs and symptoms are reminiscent of atypical connective tissue diseases such as fibromyalgia, chronic fatigue syndrome, and the process associated with exposure to silicone breast implants (SBI). Serological abnormalities including hypergammaglobulinemia and abnormal serum proteins have been reported in 45% of GWS patients (Grady, et al. *Arch. Int. Med.,* 1998, 158: 367-371).

Hundreds of explanations for GWS have been proposed. In 1994, the U.S. Secretary of Defense and the Secretary of Veterans Affairs asked the Center for Disease Control and Prevention to conduct an official scientific study exploring possible causes of GWS. The study was aimed at organizing reported symptoms into a defined case, characterizing clinical features, and evaluating risk factors. The results are described by Fukuda, et al. *J.A.M.A.,* 1998, 280: 981-988). Fukuda et al., assessed a population of Gulf War Veterans with respect to many of the proposed explanations for GWS. The study included assessment of physical symptoms; blood, urine, and stool analysis; and serological assays. Tests were conducted to detect the presence of various viruses, bacteria, mycoplasm, and parasites. Serum was tested for yellow fever, dengue, Sindbis, West Nile, and phlebotomus fever viruses (Naples and Sicilian); Toscana, Karimbad, and Isfahan viruses; *Rickettsia typhi* and *Rickettsia rickettsii; Coxiellla burnetii; Ehrlichia chaffeensis; Leishmania tropica* and *Leishmania donovani; Toxoplasma gondii; Schistosoma mansoni* and *Schistosoma haematobium; Strongyloides stercoralis; Helibacter pylori; Clostridium botulinum;* and *Bacillus anthracis.* Stool specimens were tested for red and white blood cells; ova and parasites of *Cryptosporidium parvum, Cyclospora cayetanensis, Isospora belli,* and microsporidia; enteroviruses; and bacteria strains of *Salmonella, Shigella, Yersinia, Campylobacter,* and *Escherichia coli* (0157:H7). While this study is considered an official and comprehensive report on GWS, no attempt was made to assess alternative explanations, such as adjuvant's disease.

The Persian Gulf Veterans Coordinating Board has addressed the possibility of exposures to chemical and biological agents. The Board, however, attempted to account for these illnesses without defining a molecular pathology (Persian Gulf Veterans Coordinating Board. *Arch. Int. Med.,* 1995, 155: 262-268).

One theory posits that GWS results from a dysregulation of the immune system (Hyams, et al. *Ann. Int. Med.,* 1996, 125: 398-405). The GWS patients suffer from various symptoms similar to those having autoimmune diseases, but cannot be diagnosed with a "classic" rheumatic disease. Gulf War veterans and attendant civilian personnel received a variety of immunizations in preparation for possible deployment to the Persian Gulf theater (David, et al. *Br. Med.* 1997, 314: 239-240). It has been suggested that GWS may result from an imbalance in the immune system. It was hypothesized that the imbalance may be due to an adverse reaction to a vaccination. It was noted in some patients that the onset of illness occurred within weeks of receiving a full complement of immunizations. These individuals displayed symptoms of GWS soon after vaccination and were not deployed. Other individuals were deployed, but returned home before the start of the war because of severe joint and muscle pain, as well as neurological problems. Additional personnel from the Gulf War became ill years later. These individuals, however, report the same symptoms as those who became ill only weeks after their vaccinations. The variability in the onset of disease symptoms, as well as differences in their severity, may be due to individual immune responses. Such variability is reportedly regulated at a genetic level involving the histocompatibility complex (Madzhidov, et al. *Biull. Eksp. Biol. Med.,* 1986, 102: 74-76; Lorentzen, et al. *Transplant. Proc.,* 1995, 27:1532-1534,).

A possibility exists that the immunizations administered to all personnel involved in the Gulf War may be linked to the etiology of GWS. The immunizations administered typically comprised an antigen and an immunological adjuvant. The adjuvants function to boost the protective effect of the immunization by eliciting a stronger immune response against the antigen. The adjuvants are capable of stimulating the immune system's cell-mediated and humoral responses against the antigen being administered. Cases have been reported, however, where the adjuvants cause a more generalized and indiscriminate stimulation of the immune system. This can disrupt the balance of self-regulatory mechanisms within the immune system and lead to autoimmune disease (Kleinau, et al. *Scand. J. Rheumatol.* 1995, 101: 179-181; Madzhidov, et al. *Biull. Eksp. Biol. Med.* 1986, 102: 74-76; Lorentzen, et al. *Transplant. Proc.* 1995, 27: 1532-1534).

Fibromyalgia, chronic fatigue syndrome, and the symptoms associated with exposure to silicone breast implants, have been correlated with the presence of anti-polymer antibodies (APA), particularly antibodies to polyacrylamide, in the blood of individuals suffering from these conditions (see, e.g., U.S. Pat. No. 5,834,215 to Garry et al., Edlavitch, Lancet, 1997, 349: 1170; De Jong et al., *Clin. Exp. Rheumatol.,* 2002, 20:151-160; and Bazzichi et al., *Arthritis Res. Ther.,* 2007, 9(5), online article available at the website arthritis-research(dot)com/content/9/5/R86).

There is an ongoing need to identify markers, such as antibodies, for diseases and conditions with unknown or unclear etiology. The methods and kits described herein address this need.

DEFINITIONS

The following definitions are provided in order to aid those skilled in the art in understanding the detailed description of the present invention.

"Antigenic epitope" refers to any discrete segment of a molecule, protein, or nucleic acid capable of eliciting an immune response, wherein the immune response results in the production of antibodies reactive with the antigenic epitope.

"Antipolyvinyl alcohol antibody" or "anti-PVAL antibody" refers to an antibody capable of complexing with polyvinyl alcohol (PVAL). Such an antibody may complex with PVAL, or with any antigenic epitope presented by PVAL.

"Binary complex" refers to a complex comprising an antigen (e.g., PVAL) and an antibody (e.g., anti-PVAL).

"Detectable label" refers to molecule, protein, or nucleic acid which may be detected either directly or indirectly through the use of a suitable detection agent or detection device.

"Detection agent" refers to a composition providing conditions suitable for detecting a detectable label. Such compositions often allow the observation of a calorimetric, fluorescent, or chemiluminescent signal when the detectable label is contacted with the detection agent.

"GWS" refers to Gulf War Syndrome.

"Indicator reagent" refers to a molecule, protein, or nucleic acid capable of complexing with an anti-PVA antibody. The binding component is conjugated to a detectable label.

"Polyvinyl alcohol" refers to a polymer having the general formula of $-(CH_2CHOH)_n-$, CAS Number 9002-89-5.

"Ternary complex" refers to a complex comprising an antigen (e.g., PVAL), an antibody specific for the antigen (e.g., anti-PVAL), and an indicator reagent.

"APA" refers to antipolymer antibodies, e.g., as described in U.S. Pat. No. 5,834,215 to Garry et al., which is incorporated herein by reference.

SUMMARY

An immunoassay for detecting anti-polyvinyl alcohol (anti-PVAL) antibodies is described herein. As disclosed herein, anti-PVAL antibodies have been found in serum samples of individuals who also are positive for antipolymer antibodies, which have been associated with fibromyalgia. It is believed that anti-PVAL antibodies may also be associated with GWS, based on preliminary results from samples from individuals diagnosed with GWS. The anti-PVAL immunoassay typically comprises several steps, as outlined below.

Immunoassay techniques and methods generally known to those skilled in the art for detecting human antibodies are described in Antibodies: A Laboratory Manual by Ed Harlow and David Lane (1988) Cold Spring Harbor Laboratory, Cold Spring Harbor, N.Y. generally including homogenous and heterogeneous assay configurations. Currently, no known method exists for detecting serum antibodies to PVAL.

An exemplary embodiment of a method for detecting anti-PVAL antibodies in a sample (e.g., a bodily fluid, such as blood or serum) comprises the steps of combining polyvinyl alcohol (PVA) with a sample to be tested for the presence of an anti-PVAL antibody to form a complex between the PVA and anti-PVAL antibodies in the sample (e.g., for a few seconds to a few hours). Generally the test sample is a bodily fluid or tissue sample, typically a serum sample. An indicator reagent is then contacted with the complex to indicate the presence or absence of an anti-PVAL antibody in the sample, e.g., by imparting a color or other detectable signal to the complex. In some embodiments, the PVAL can be bound to a solid phase (e.g., nitrocellulose, polyvinylidene difluoride (PVDF) and nylon. The indicator reagent comprises a binding compound that is specific for a human antibody and which is conjugated to a detectable label. The binding reagent is combined with the sample and PVAL a labeled ternary complex, e.g., on the solid support, such as nitrocellulose, polyvinylidene difluoride (PVDF), nylon, polypropylene, polystyrene, polyvinylchloride, polyamide, polycarbonate, polyether, polymethyl methacrylate, nitrocellulose, polyvinylidene difluoride, agarose, or metal. Optionally, the solid support can be in the form of a membrane, plastic beads, agarose beads, or magnetic beads. The solid support also can be a strip or microtiter plate, and the PVAL is bound to specified regions of the strip or wells of the plate.

In some embodiments, the indicator reagent can comprise a binding member that is specific for a human antibody and which is conjugated to a detectable label (e.g., a protein, an enzyme, a radioisotope, a nucleic acid segment, a fluorochrome, or a fluorescent protein), and the indicator reagent is combined with the sample and PVAL to form the labelled ternary complex on the solid phase support. Suitable enzyme labels include, e.g., horseradish peroxidase, alkaline phosphatase, or beta-galactosidase. Enzyme labels can be used to catalyze the conversion of a non-chemiluminescent reagent into a chemiluminescent product, or to catalyze the conversion of a non-colorimetric reagent to a colorimetric product.

In another aspect, a kit for use in detecting an anti-PVA antibody comprises PVAL attached to a support material; and an indicator reagent comprising a binding member that is specific for a human antibody and which is conjugated to a detectable label. The binding member is capable of forming a complex with an anti-PVA antibody. Optionally, the kit further comprises a wash composition for separating non-complexed materials from support material. In some kit embodiments the detectable label is an enzyme and the indicator reagent affords a colorimetric or chemiluminescent signal in the presence of the enzyme. The solid support of the kit can comprise, e.g., nitrocellulose, polyvinylidene difluoride (PVDF), and nylon, or any of the other materials described above with respect to the method aspect (e.g., polypropylene, polystyrene, polyvinylchloride, polyamide, polycarbonate, polyether, polymethyl methacrylate, nitrocellulose, polyvinylidene difluoride, agarose, metal, membranes, plastic beads, agarose beads, or magnetic beads). In a preferred embodiment, the solid support of the kit is in the form of a strip or a microtiter plate.

BRIEF DESCRIPTION OF THE DRAWINGS

The following drawings form part of the present specification and are included to further demonstrate certain aspects of the present invention. The methods described herein may be better understood by reference to the drawings in combination with the detailed description of specific embodiments presented herein.

DETAILED DESCRIPTION

Figure 1:
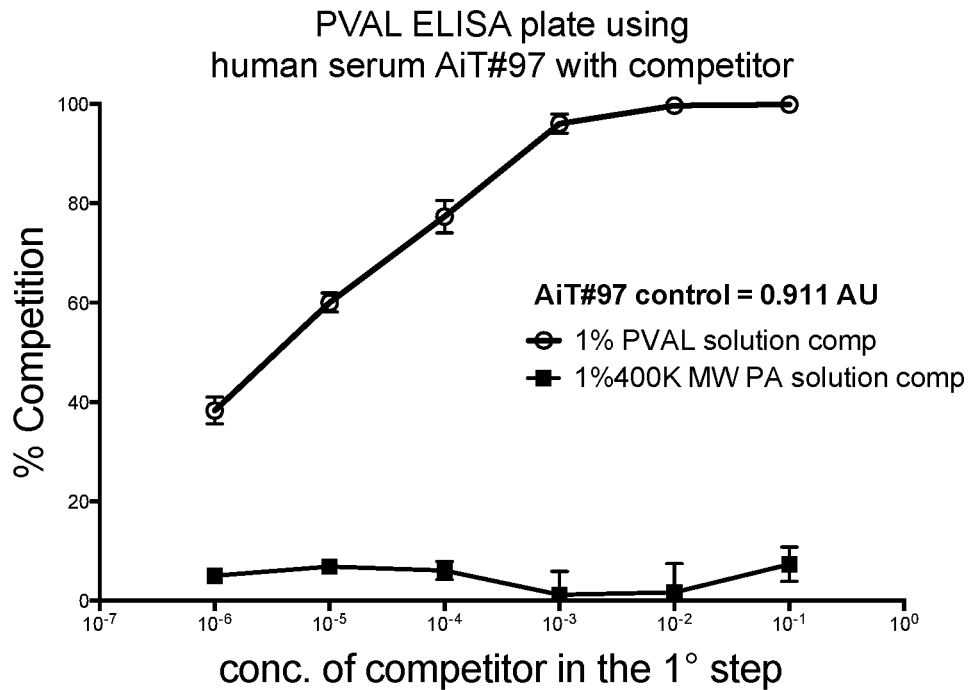
FIG. 1 shows a plot of APVAL ELISA data for a serum sample that was positive for both anti-PVAL and antipolymer antibodies with 400 MW polyacrylamide (top data plot) and polyvinyl alcohol (bottom data plot) as competitors.

Certain embodiments of methods and kits for detecting anti-PVAL antibodies are described herein. It should be understood that the present disclosure is to be considered as an exemplification of certain aspects, features and principals of the invention described herein, and is not intended to limit the invention to the specific exemplary embodiments that are described.

A method of detecting anti-PVAL antibodies includes the steps of (a) mixing PVAL with a test sample of body fluid (e.g., serum) for a time sufficient to form a binary complex between the PVAL and an anti-PVAL antibody in the sample, and (b) combining an indicator reagent with the binary complex to form a ternary complex therewith, and then detecting the presence of the ternary complex. The method can be used, for example, as a tool to aid in diagnosing patients with, e.g., fibromyalgia. In addition, a preliminary evaluation of serum samples from GWS patients afforded positive results for anti-PVAL using the methods described herein.

A representative procedure for detecting anti-PVAL antibodies is an anti-PVAL antibody (APVAL) line blot analysis, which is described in more detail below. Alternatively, anti-PVAL antibodies can be detected by other binding assays which are generally categorized into two major classes, namely, homogenous and heterogeneous assays.

Homogenous assay configurations do not require the separation of the test solution and the indicator reagent prior to the detection of the indicator reagent or binding complexes. This broad classification includes many formats such as agglutination and precipitation assays as well as others known to those skilled in the art for the detection of antibodies and antigens.

The methods described herein can also be carried out using a solid phase sandwich assay (a heterogeneous assay) to detect the presence or amount of anti-PVAL antibodies in the test sample. A capture reagent typically involving a specific binding member such as the PVAL antigen is affixed to the solid phase material. A test sample is incubated with the capture reagent for a period of time under conditions sufficient for the formation of specific complexes between anti-PVAL antibodies in the test sample and the PVAL antigen. The solid phase material can then be washed with a buffer solution including any buffer conventionally known to remove unbound materials present in the test sample. The resultant complexes are then incubated with an indicator reagent, such as a second, labeled PVAL antigen, for a period of time and under condition sufficient for the formation of a ternary complex. The unreacted indicator reagent is removed by again washing the solid phase with a buffer solution. The quantity of indicator reagent bound to the solid phase is then measured by a technique compatible with the label component of the indicator reagent. If quantitated, the amount of indicator reagent bound to the solid phase is proportional to the quantity of test sample anti-PVAL antibody bound to the solid phase. The reagents of the method can be mixed simultaneously or added sequentially either singly or in combination.

The solid phase material can include any suitable chromatographic bibulous, porous or capillary material or other conventional solid material well known to those skilled in the art, used to immobilize specific binding members. Specifically, the solid phase material can include, e.g., a fiberglass, cellulose or nylon pad for use in a flow through assay devices having one or more layers containing one or more of the assay reagents; a dipstick for a dip and read assay; a test strip for chromatographic (i.e., paper or glass fiber) or thin layer chromatographic (i.e., nitrocellulose) techniques in which one or all of the reagents are contained in separate zones of a single strip of solid phase material; or an absorbent material well known to those skilled in the art. These solid phase materials also can include, without limitation, polyacrylamide beads, polystyrene beads or tubes, magnetic beads, a microtiter plate or a glass or plastic test tube.

Natural materials, synthetic materials, or naturally occurring materials that are synthetically modified, can also be used as a solid phase material including polysaccharides, i.e., cellulose materials such as paper, and cellulose derivatives such as diazobenzyloxymethylcellulose, nitrocellulose, 2-aminophenylthioetheylcellulose, and cellulose acetate; silica; silicon particles; inorganic materials such as deactivated alumina, or other inorganic finely divided material uniformly dispersed in a porous polymer matrix, with polymers such as vinyl chloride, vinyl chloride polymer with propylene, and vinyl chloride polymer with vinyl acetate; cloth, both naturally occurring (i.e., cotton) and synthetic (i.e. nylon); porous gels such as silica gel, agarose, dextran, and gelatin; polymeric films such as polyacrylates; protein binding membranes; and the like. The solid phase material should have reasonable strength or strength that can be provided by means of a support, and it should not interfere with the production of a detectable signal.

The capture reagent typically involves a specific binding member that has been bound to a solid phase material. The specific binding member can directly or indirectly bind the antibody, antigen or indicator reagent and which is bound or is capable of being bound to a solid phase, or is capable of being precipitated such that the capture binding member can be separated from the test sample and other assay reagents by any means. The capture reagent is not limited to a capture binding compound that is bound to an insoluble solid phase material. In an agglutination assay, the capture binding compound of the capture reagent can be bound to a soluble carrier such as bovine serum albumin.

The specific binding member is a member of a specific binding pair, i.e., two different molecules wherein one of the molecules through chemical or physical means specifically binds (as opposed to nonspecific binding) to the second molecule. In addition to antigen and antibody, specific binding pairs, in which either one may be immobilized and bind to the test sample, may include: biotin and avidin; carbohydrates and lectins; complementary nucleotide sequences; complementary peptide sequences; effector and receptor molecules; enzyme cofactors and enzymes; enzyme inhibitors and enzymes; a peptide sequence and an antibody specific for the sequence or the entire protein; polymeric acids and bases; dyes and protein binders; protein A and antibodies; protein G and antibodies; and the like.

Furthermore, specific binding pairs can include materials that are analogs of the original specific binding member, for example an analyte-analog. An analyte is defined as either the PVAL antigen or the anti-PVAL antibody. If the specific binding member is an immunoreactant, it can be an antibody, an antigen, a hapten, or a complex thereof. Further, antibodies can be monoclonal or polyclonal, a recombinant protein or antibody, a mixture or fragment thereof, as well as a mixture of an antibody and other specific binding members. The details of the preparation of such antibodies and their suitability for use as specific binding members are well known to those skilled in the art.

An indicator reagent comprises a detectable label that is directly or indirectly attached to a specific binding member, which is capable of directly or indirectly binding to the antibody or antigen to indicate the presence or absence or amount of antibody or antigen bound to the solid support. A variety of different indicator reagents can be formed by varying either the label or the specific binding member. In general the indicator reagent is detected after it has formed a complex with either the antibody or antigen or a complementary specific binding member. Optionally, the unbound indicator reagent can also be detected.

A label can refer to any substance that is attached to a specific binding member and which is capable of producing a signal that is detectable by visual or instrumental means. Various suitable labels for use in the present invention can include chromogens; catalysts; fluorescent compounds; chemiluminescent compounds; radioactive labels; direct visual labels including: colloidal metallic and nonmetallic particles, dye particles, enzymes or substrates, or organic polymer latex particles; liposomes or other vesicles containing signal producing substances (capable of reacting with another assay reagent, the antibody or antigen to produce a signal detectable by visual or instrumental means); and the like.

A method of the present invention can also be carried out using competitive assay formats. In a solid phase competitive assay, the capture reagent again typically involves a specific binding member that has been affixed to a solid phase material and which is contacted with both the test sample and an indicator reagent. The indicator reagent, however, can be formed from an analyte or analyte-analog that has been conjugated with a label. A binding reaction occurs and results in the formation of complexes of (1) immobilized capture reagent/analyte complex and (2) immobilized capture reagent/indicator reagent complex. Alternatively, the immobilized specific binding member can be an analyte or analyte-analog with which the test sample analyte competes for binding to the indicator reagent. In the competitive assay, the amount of label on the solid phase is inversely related to the amount of analyte in the sample. Thus, a positive test sample will generally decrease in signal.

In one embodiment of the method described herein, the PVAL antigen is applied to a nitrocellulose support, which is cut into strips. The strips are incubated for one hour with a test sample, and an indicator reagent is then added to the strips thereby enabling the anti-PVAL antibody to be visualized.

An APVAL line blot analysis detects anti-PVAL antibodies in test sera with increased specificity and sensitivity over any other immunoassays. Anti-PVAL antibodies specifically respond to the PVAL and can be identified over, e.g., previously described antipolymer antibodies (e.g., antibodies to polyacrylamide or silicone polymers) utilizing the line blot analysis. The APVAL antibody line blot analysis typically involves the addition and incubation of several different reagents. A variety of different buffer and washing solutions can be used to stabilize the reagents and to remove excess reagents or test sample from the reaction. As is well known to those skilled in the art, modifications can be made in the buffer and washing solutions, as well as in the reaction times.

The line blot assay format (also referred to herein as a "strip" assay) utilizes PVAL antigen applied in stripes (bands) onto a nitrocellulose paper matrix. The control human sera used in these strip assays show consistent signal on these assay strips and is used as a calibrator between runs and for determining the relative strength of signal for the unknowns; typically one uses three controls ranging in signal from: strongly positive (++) control, positive (+) control and negative (−) control. The controls are also used to provide a semi-quantitative assessment of the relative concentration of anti-PVAL antibody in the serum sample.

To begin with, the PVAL antigen strips are rinsed with a wash buffer and then blocked with a prepared milk-based blocking solution (milkblock). The blocking solution is aspirated off and individual human serum samples (controls and unknowns) are diluted into the previously described milkblock buffer and applied to the strips and allowed to incubate with rocking. After the incubation time, the human serum solutions are aspirated off and the strips are washed thoroughly using the aforementioned wash buffer. A solution containing biotin-goat anti-human IgG (in milkblock buffer) is then added and the treated strips are allowed to incubate with rocking. The biotin-goat anti-human solution is aspirated off and the strips are washed thoroughly with the wash buffer and a solution of horseradish peroxidase in phosphate buffered saline (PBS) containing bovine serum albumin (BSA) is subsequently applied to the strips with rocking. After the incubation time the horseradish peroxidase solution is aspirated off, the strips washed thoroughly with the wash buffer, and a developing solution containing 4-chloro-1-naphthol, methanol, PBS and hydrogen peroxide is added to the strips and allowed to incubate with rocking. Finally, after the development step has been completed, the solution is aspirated off and the strips are washed with wash buffer, followed by reagent grade water, and are then allowed to dry overnight. The presence of a blue/purple color in the strips indicates the presence of anti-PVAL antibodies in the tested serum sample. The following day, the strips are mounted onto paper and the signal of unknown sera testing strips is determined by visual inspection of color intensity. Typically, a rating of negative (−), weakly positive (+/−), positive (+) or strongly positive (++) is assigned and based off of the signal intensity of the sample run as compared to the controls run in parallel (other relative intensity scales, such as 0, +1, +2, +3, +4 may, also be used as long as there are correlated controls available).

As discussed in detail herein, anti-PVAL antibodies have been found in in sera of people who also are positive for antipolymer antibodies associated with fibromyalgia and fibromyalgia-like symptoms and conditions. The APVAL line blot analysis can be utilized to objectively detect an immunological response to PVAL. Identification of anti-PVAL in serum may provide a useful tool, e.g., to aid in the identification or diagnosis of patients with fibromyalgia, or as a potential marker for susceptibility to fibromyalgia in otherwise healthy individuals.

In the present methods, the test sample can be obtained from any naturally occurring or artificially formed liquid test medium suspected of containing the anti-PVAL antibody, or PVAL antigen. The test sample is generally a biological fluid or dilution thereof from which an anti-PVAL antibody or PVAL antigen can be detected, including: serum; whole blood; plasma; body fluid; saliva; amniotic and cerebral spinal fluids; and the like.

In addition to a nitrocellulose support, other materials such as polyvinylidene difluoride (PVDF) and nylon can be alternative membrane sources. The APVAL line blot assay has also been adapted to a standard 96-well polystyrene enzyme linked immunosorbent assay (ELISA) format. The APVAL line blot is also amenable to adaptation to other immunological assays including latex agglutination, antibody capture assays, radioimmunoprecipitation assays (RIPA), polystyrene bead based enzyme immunoassays (EIA), and particle concentration fluorescence immunoassays (PCFIA).

ELISA (enzyme-linked immunosorbent assay) is a plate-based assay technique for detecting and quantifying proteins, including antibodies. In an ELISA, the PVAL antigen is immobilized to a solid surface of a microtiter plate at various know dilutions in a preselected pattern. The coated plate is then contacted with a serum sample to be analyzed. If antibodies for PVAL are present then they attach to the antigens in the wells of the plate. Once the antibodies are attached to the antigen, the resulting complex is visualized by first contacting the plate with a marker antibody that is specific to all human antibodies, and which includes a visualizable label compound bound to the antibody. The plate is then rinsed with a buffer to remove any unbound material. When the marker antibody comes into contact with a human antibody bound to the antigen (PVAL) on the plate (i.e., the anti-PVAL antibody) the marker antibody binds to the already bound anti-PVAL antibody. The plate is then rinsed again with a buffer to remove any unbound marker antibody material. Finally plate is contacted with a visualizing compound (e.g., a dye or dye precursor) that can react with the label to form a measureable product (e.g., a product that can be quantitatively measured by spectroscopic techniques). In some cases, the measureable product is colored. Thus, when an anti-PVAL antibody is present in the serum sample, the label reacts with the visualizing compound causing the liquid in the wells of the microtiter plate to produce the measurable product in an amount that is proportional to the amount of anti-PVAL antibody present in the serum sample. For example, the label of the marker antibody can be an enzyme, and detection is accomplished by assessing the conjugated enzyme activity via incubation with a substrate to produce a measureable product.

The APVAL ELISA analysis can be utilized to objectively detect an immunological response to PVAL. Identification of anti-PVAL in serum may provide a useful tool, e.g., to aid in the identification or diagnosis of patients with fibromyalgia, or as a potential marker for susceptibility to fibromyalgia in otherwise healthy individuals.

The ELISA assay format utilizes PVAL antigen coated onto an ELISA plate (96-well) substrate (polystyrene or similar). To begin with, the plate wells are blocked with a prepared milkblock buffer. The blocking solution is aspirated off and the wells are washed with wash buffer (containing NaCl, TWEEN 20 surfactant, TRIS surfactant, thimerosal and water) using a plate washer. Human serum samples are diluted into the previously described milkblock buffer (e.g., at about 1:500, 1:1000, and/or 1:1600 dilution, v/v) and applied to the wells. Afterward, the human serum solution is aspirated off (using a plate washer) and the wells are washed thoroughly using the prepared wash buffer and plate washer. Next, a solution containing biotin-goat anti-human IgG (GaHIgG) in the milkblock buffer (typically about 1:1000 dilution, v/v) is then added to the wells and allowed to incubate (e.g., about 1 hour, room temp). The wells are washed with the plate washer with the aforementioned wash buffer and a solution of horseradish peroxidase (e.g., in PBS containing BSA, typically about 1:1000 dilution, v/v) is subsequently applied to the wells. After incubation (typically about 1 hour), the peroxidase solution is aspirated off and the wells washed with the plate washer using the wash buffer, and a developing solution (TMB SUREBLUE developer, comprising 3,3',5,5'-tetramethylbenzidine in a mildly acidic buffer) is added and allowed to incubate (e.g., about 30 minutes, room temp). Presence of positive signal develops as a blue solution with the intensity increasing with concentration of the detected species. Finally, after the development incubation step has been completed, an acidic solution (1N HCl or similar) is added to the wells, turning them yellow and stopping development of signal. Subsequently, optical density measurements of absorbance of the wells are read at 450 nm. The results are reported as Absorbance Units (AU). In the absence of a specified standardized cutpoint, a general absorbance greater than about three times the background is considered presumptively positive. Those samples can then be run through an immunodepletion procedure to establish specificity of the positive signal.

In another aspect, the assay reagents are provided in test kit. A test kit to detect antipolymer antibodies typically contains a support material upon which polymer antigen is immobilized and optionally includes an appropriate supply of a suitable indicator reagent, buffer solutions and a suitable indicator reagent. The kit also includes a binding member that is specific for human antibody, conjugated to a detectable label, and may provide a calorimetric or chemiluminescent signal in the presence of an enzyme label.

A test kit to detect PVAL antigen typically contains a solid phase material upon which anti-PVAL antibody is immobilized or upon which components of the test sample can be immobilized (i.e., direct immobilization of the antigen upon the solid phase), and optionally includes appropriate amounts of a suitable indicator reagent, buffer and washing solutions. Other components such as stabilizers and preservative agents can also be present in the kit and/or in the reagents.

Methods generally known to those skilled in the immunological arts are described in Antibodies: A laboratory Manual by Ed Harlow and David Lane, (1988), Cold Spring Harbor Laboratory, chapters 12 and 14 and are hereby incorporated by reference.

The following examples are provided to illustrate certain aspects and features of the methods described herein and are not meant to be limiting

EXAMPLE 1

Detection of Anti-PVAL Antibodies by ELISA in Serum Samples

A. Serum samples

Serum samples from 180 human females (identified herein as AiT#1 through AiT#180) were obtained from SeraCare Life Sciences, Milford, Mass.

B. Evaluations of a serum sample that was positive for APA and APVAL with APVAL ELISA and APA ELISA with PVAL and polyacrylamide solutions as competitors.

General ELISA procedure:

The ELISA assay format utilizes PVAL antigen (or polyacrylamide, PA, antigen for APA ELISA) coated onto an ELISA plate (96-well) substrate (polystyrene or similar). To begin with, the plate wells are blocked with a prepared milkblock buffer for 2 hours, room temp (containing dry milk, water, heat treated goat serum albumin, TRIS surfactant, NaCl, thimerisol and azide). The blocking solution is aspirated off and the wells are washed 3× with wash buffer (containing NaCl, TWEEN 20 surfactant, TRIS surfactant, thimerosal and water) using a plate washer. Human serum samples are diluted into the previously described milkblock buffer (e.g., at about 1:500, 1:1000, and/or 1:1600 dilution, v/v) and applied to the wells (about 100 µL for about 1 hour, room temp). Afterward, the human serum solution is aspirated off (using a plate washer) and the wells are washed thoroughly (3×) using the prepared wash buffer and plate washer. Next, a solution containing GaHIgG in the milkblock buffer (about 100 µL, about 1:1000 dilution, v/v) is then added to the wells and allowed to incubate (about 1 hour, room temp). The wells are washed 3× with the plate washer with the aforementioned wash buffer and a solution of horseradish peroxidase (in PBS containing BSA, about 1:1000 dilution, v/v) is subsequently applied to the wells (about 100 µL) and the plate is incubated (e.g., about 1 hour, room temp). After incubation, the peroxidase solution is aspirated off and the wells washed with the plate washer (3×, wash buffer). A developing solution (TMB SUREBLUE developer) is then added (about 100 µL) and the plate is incubated (e.g., about 30 minutes, room temp). The presence of positive signal develops as a blue solution with the intensity increasing with concentration of the detected species. Finally, after the development incubation step has been completed, about 50 µL of an acidic solution (1N HCl or similar) is added to the wells, turning them yellow and stopping development of signal. Subsequently, optical density measurements of absorbance of the wells are read at 450 nm. The results are reported as Absorbance Units (AU). In the absence of a specified standardized cutpoint, a general absorbance greater than about three times the background is considered presumptively positive. Those samples can then be run through an immunodepletion procedure to establish specificity of the positive signal.

Competition Experiments:

Using the general ELISA procedure described above for the APA and PVAL testing schemes, competition experiments were performed to verify the specificity of the two antibodies detected within the same human serum sample. In this example, human serum sample AiT#97 showed strongly positive signal on both the APA ELISA and the PVAL ELISA tests. As a follow up, the experiments were repeated on the respective ELISA well formats with the addition of free antigen (PA or PVAL) in solution as a competitor.

The APA ELISA used a 1:400 dilution of human serum, a 1:1000 dilution (v/v) of GaHIgG and a 1:1000 (v/v) dilution of horseradish peroxidase-conjugated streptavidin (HRP-strep) within the testing scheme. The PVAL ELISA used a 1:20,000 (v/v) dilution of human serum, a 1:2000 (v/v) dilution of GaHIgG and a 1:16,000 (v/v) dilution of HRP-strep within the testing scheme.

Figure 2:
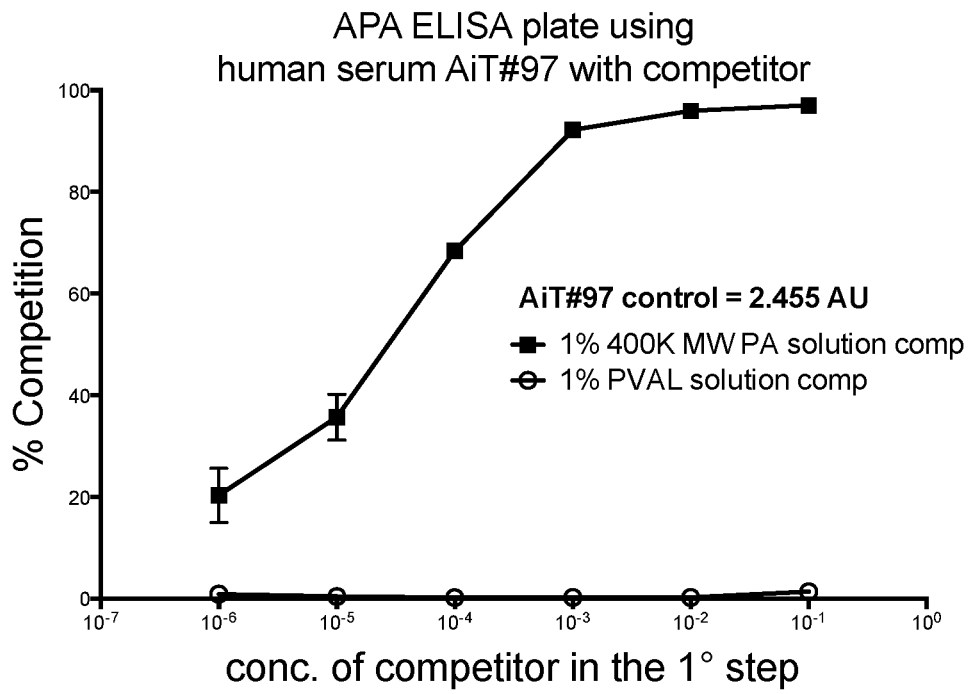
FIG. 2 shows a plot of APA ELISA data for a serum sample that was positive for both anti-PVAL and antipolymer antibodies in the presence of 400 MW polyacrylamide (bottom data plot) and polyvinyl alcohol (top data plot) as competitors.
Figure 3:
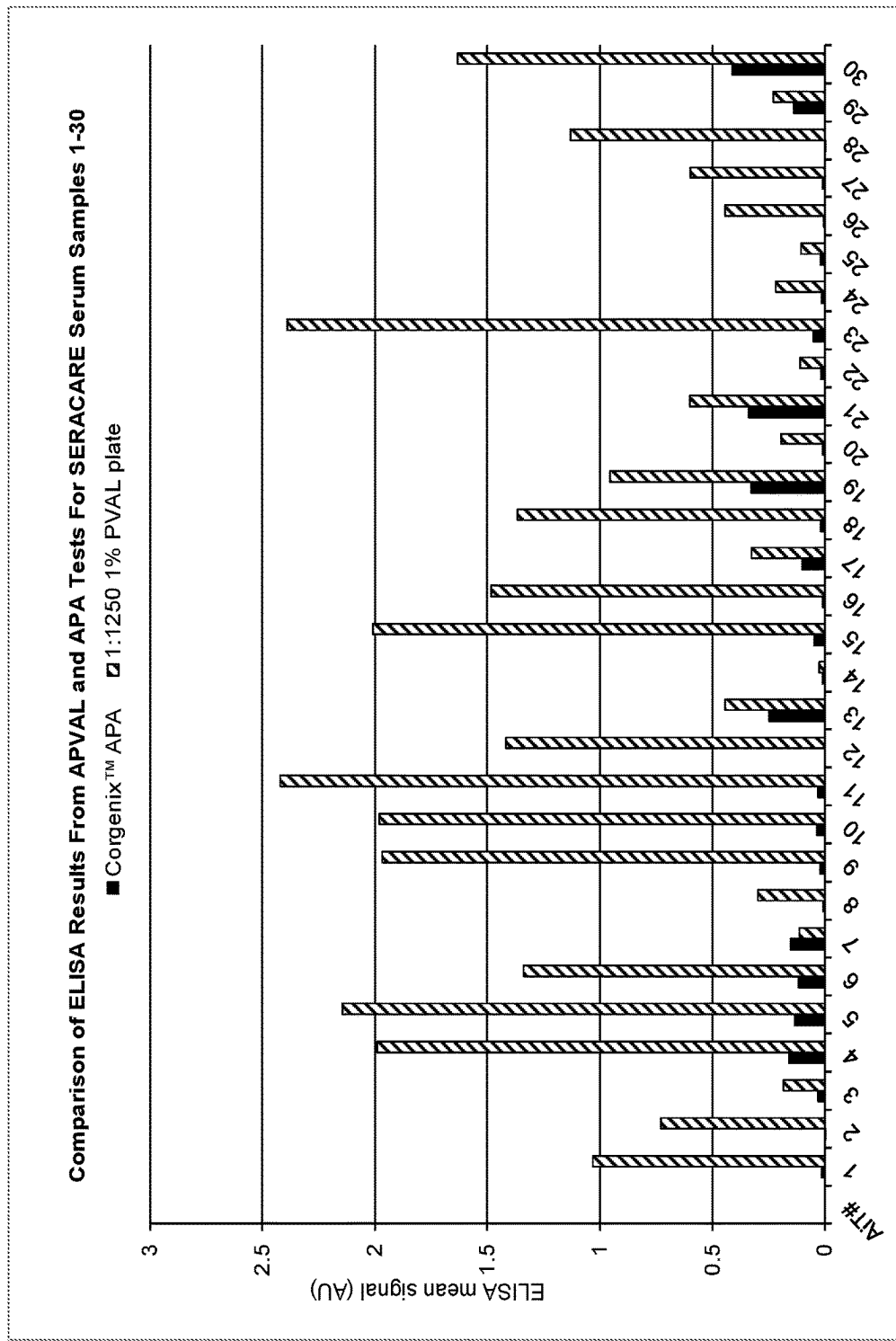
FIG. 3 shows a comparison of ELISA results from APVAL and APA tests for SERACARE serum samples AiT#1-30.
Figure 4:
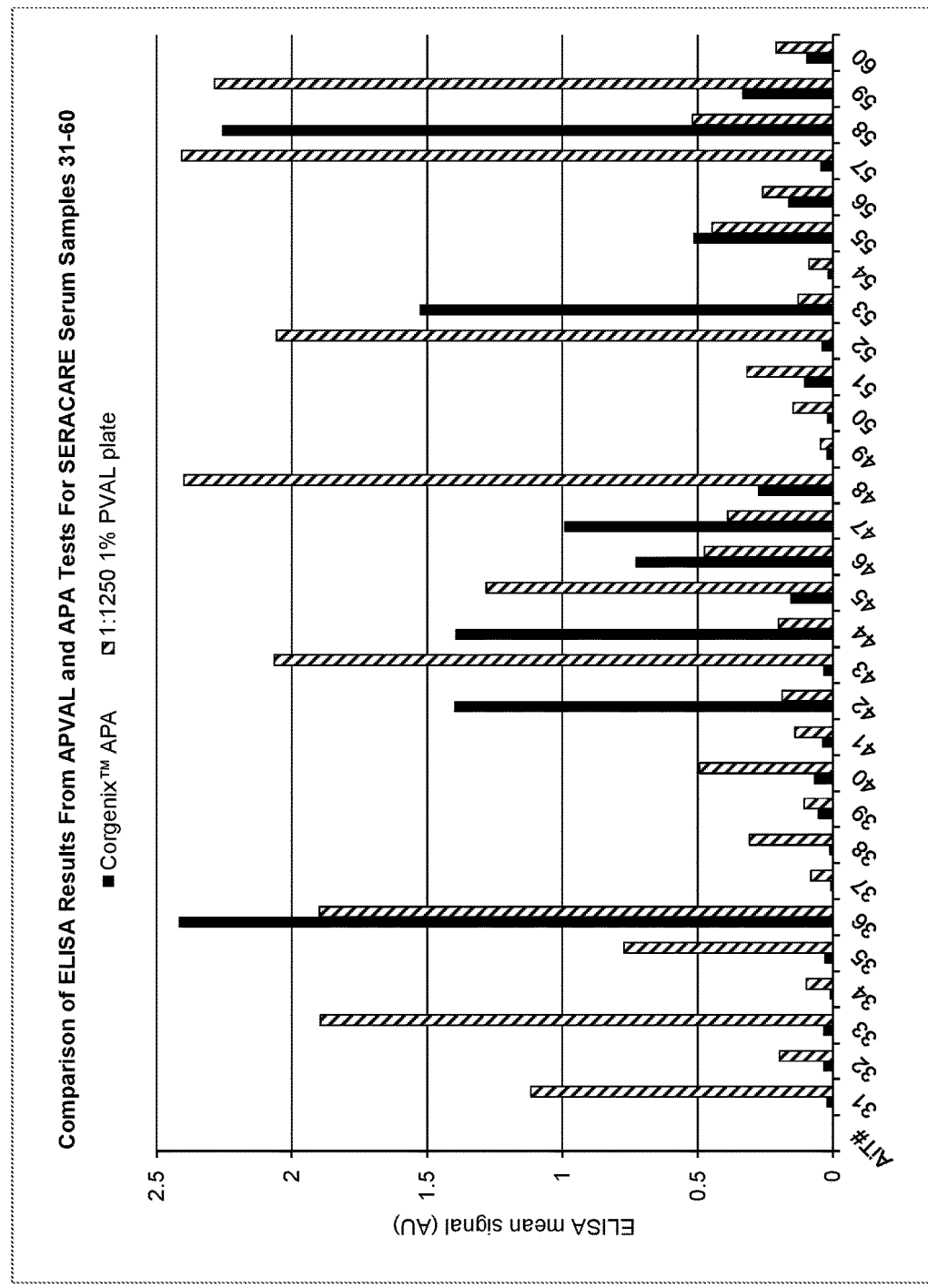
FIG. 4 shows a comparison of ELISA results from APVAL and APA tests for SERACARE serum samples AiT#31-60.
Figure 5:
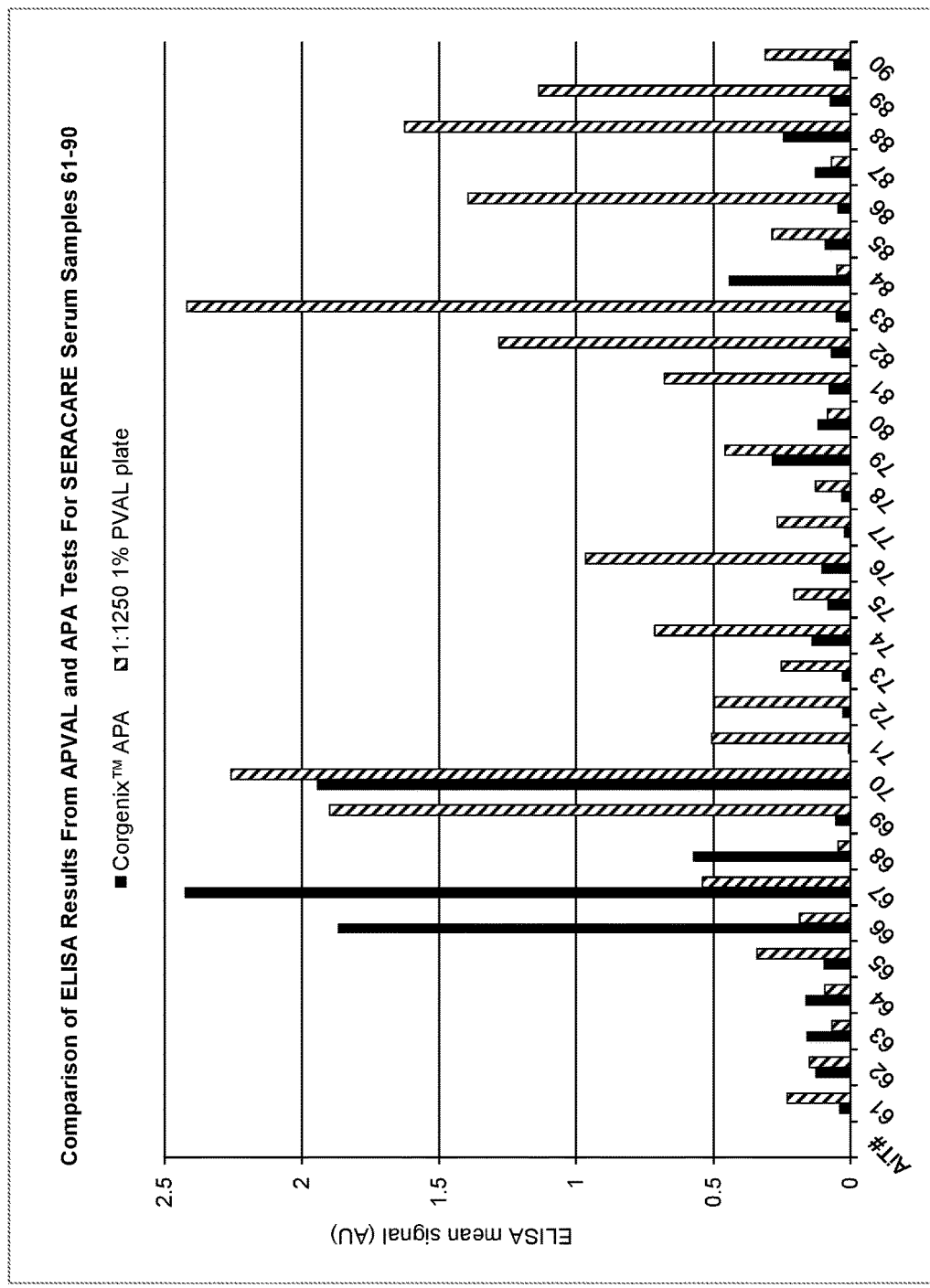
FIG. 5 shows a comparison of ELISA results from APVAL and APA tests for SERACARE serum samples AiT#61-90.
Figure 6:
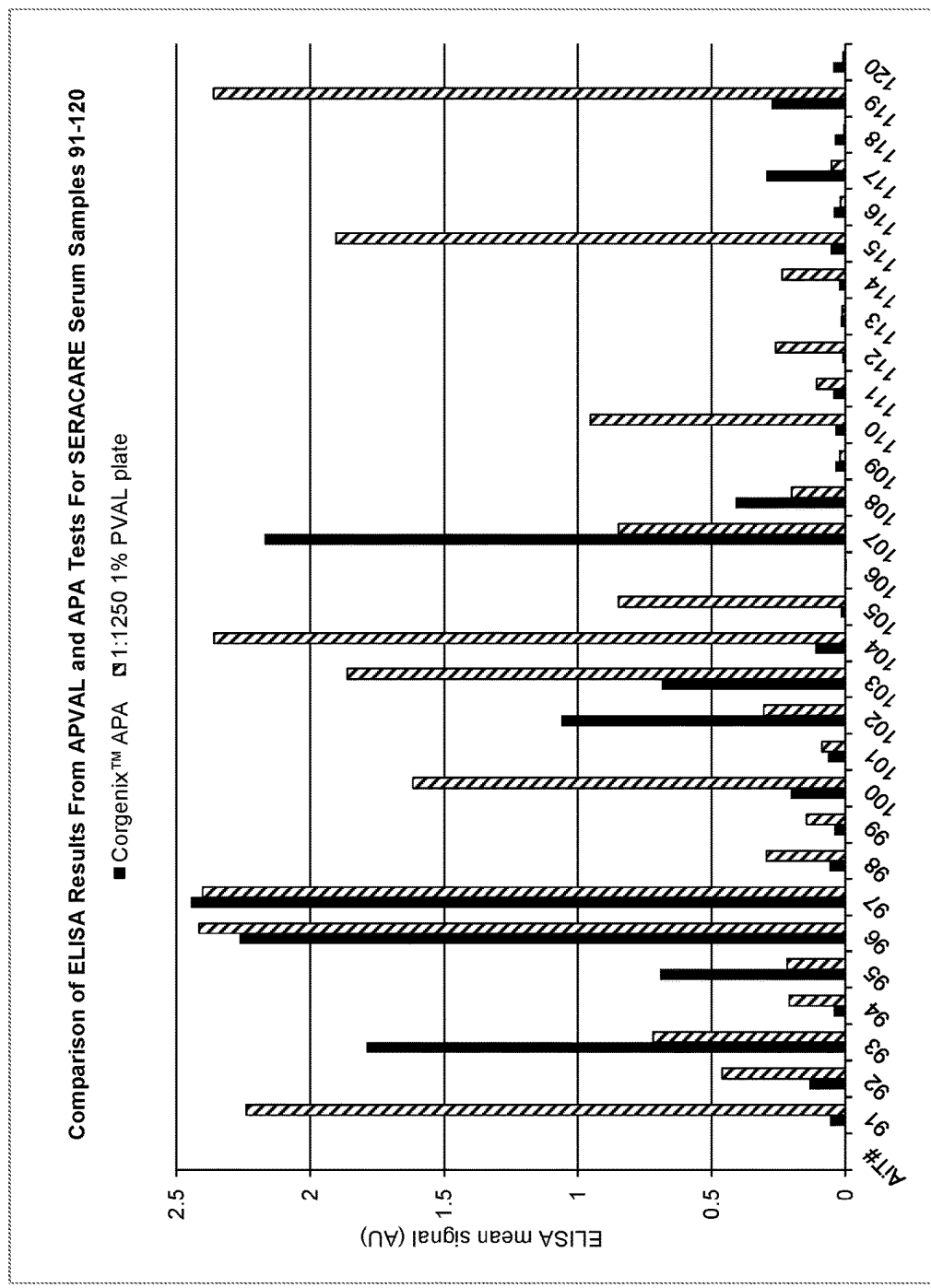
FIG. 6 shows a comparison of ELISA results from APVAL and APA tests for SERACARE serum samples AiT#90-120.
Figure 7:
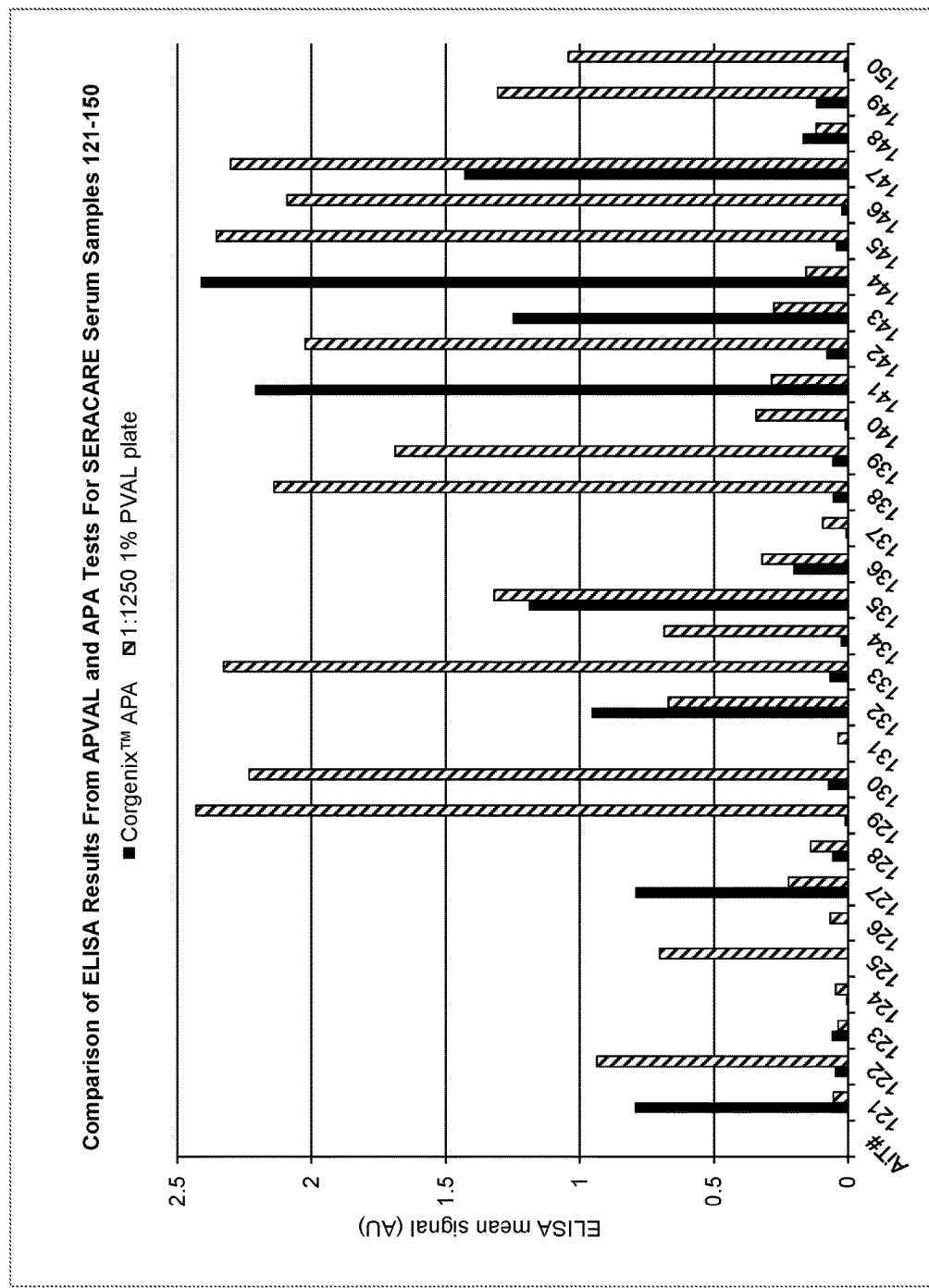
FIG. 7 shows a comparison of ELISA results from APVAL and APA tests for SERACARE serum samples AiT#121-150.
Figure 8:
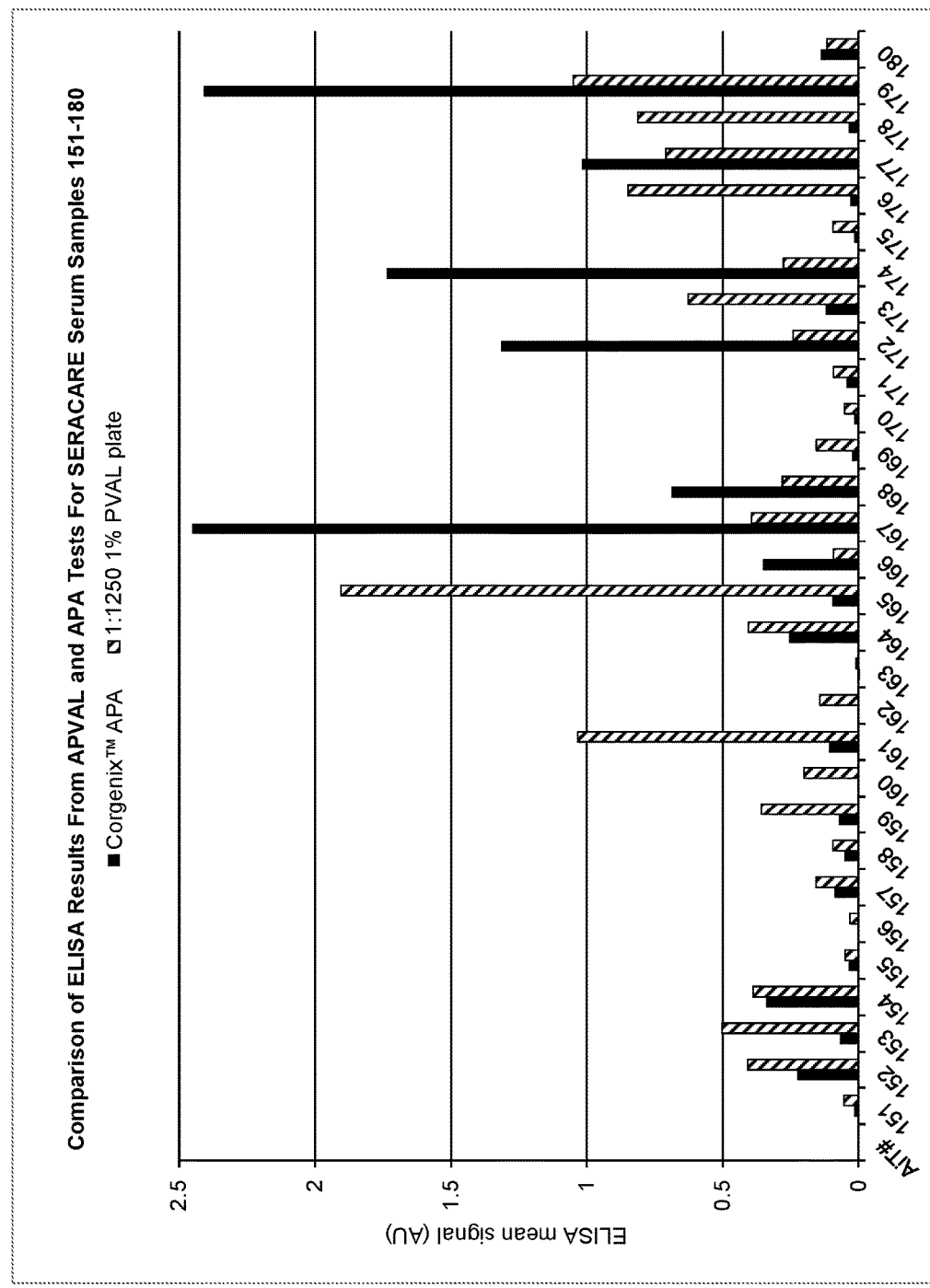
FIG. 8 shows a comparison of ELISA results from APVAL and APA tests for SERACARE serum samples AiT#151-180.

In each case a dilution series of a 1% polymer solution (ranging from about 1:10 to about 1:1 molar dilution, v/v) was added to the dilution of human serum in milkblock (v/v) as a competitor, mixed and allowed to incubate for 45 minutes (room temp) prior to application to the ELISA well. In the competitive incubation step, the free polymer in solution binds to any corresponding antibodies in the serum sample in solution and effectively immunodepletes the amount of free antibody available later to bind to the antigen coated on the plate wells. This results in a decreasing the ELISA signal as compared to the non-competitive control. FIG. 1 and FIG. 2 show that while there are antibodies present in the serum sample that recognize both polyacrylamide (APA ELISA) and polyvinyl alcohol (PVAL ELISA), these antibodies do not share related epitopes and do not recognize the heterologous antigen counterpart (i.e., antibodies detected in the APA ELISA recognize polyacrylamide and not polyvinyl alcohol, and antibodies detected in the PVAL ELISA recognize polyvinyl alcohol and not polyacrylamide). The results demonstrate that that the PA and PVAL antibody signals are real, specific, and independent from one another.

C. Evaluation of 180 serum samples using APVAL ELISA and APA ELISA.

FIGS. 2-8 show a survey of a human sera from healthy donors tested for anti-PVAL and antipolymer (anti-PA) antibodies. Each sample was run in triplicate and within the general protocol for the APA and PVAL ELISA schemes in separate runs. The data were compiled and the results shown in a side-by-side graph format. The APA ELISA format utilized the CORGENIX testing kit and a 1:101 dilution of human serum (v/v). The PVAL ELISA format used a 1:20,000 dilution of human serum (v/v), a 1:2000 dilution of GaHIgG (v/v) and a 1:16,000 dilution of HRP-strep (v/v) for the testing scheme.

These data demonstrate that within the sera samples tested from this population, there are two distinct and independent positive groups of antibodies being detected. Those testing positive for antibodies specific to APA (e.g., using the CORGENIX APA kits), which has been associated with fibromyalgia an another group testing positive for antibodies specific to polyvinyl alcohol. While there is some overlap between the two groups, there is no direct correlation; and those samples with both antibodies present show that those antibodies are independent from each other in the serum sample. The data is FIGS. 2-8 show that APVAL is a new seroimmunological marker that is independent from APA. Given the overlap in the presence of APA and APVAL in many samples, APVAL could be a useful tool to aid in identifying another subset of fibromyalgic-like symptom-positive population that may be overlooked by testing for APA alone. Additional competitive assays using a 1:10 (v/v) dilution of a 1% antigen solution as the competitor showed that, in all cases, complete competition was observed (indicating the presence of a specific antibody to polyvinyl alcohol).

EXAMPLE 2

Detection of Anti-Pval Antibodies by Strip Analysis

General Procedure:

The strip assay utilizes PVAL antigen applied in stripes (bands) onto a nitrocellulose paper matrix. The control human sera used in these strip assays show consistent signal on these assay strips and is used as a calibrator between runs and for determining the relative strength of signal for the unknowns; typically one uses three controls ranging in signal from: strongly positive (++) control, positive (+) control and negative (−) control. The controls are also used to provide a semi-quantitative assessment of the relative concentration of anti-PVAL antibody in the serum sample.

To begin with, the PVAL antigen strips are rinsed with a wash buffer (containing NaCl, TWEEN 20 surfactant, TRIS surfactant (i.e., tris(hydroxymethyl)-aminomethane), thimerosal, and water) and then blocked with a prepared milkblock buffer for about 45 minutes with rocking (containing dry milk, water, heat treated goat serum albumin, TRIS surfactant, NaCl, thimerisol and azide). The blocking solution is aspirated off and individual human serum samples (controls and unknowns) are diluted into the previously described milkblock buffer and applied to the strips and allowed to incubate with rocking (about 90 minutes, room temp). After the incubation time, the human serum solutions are aspirated off and the strips are washed thoroughly (3×, about 5 minutes each) using the aforementioned wash buffer. A solution containing biotin-goat anti-human IgG (in milkblock buffer, about 1:1000 dilution v/v) is then added and the treated strips are allowed to incubate with rocking (about 60 minutes, room temp). The biotin-goat anti-human solution is aspirated off and the strips are washed thoroughly (3×, about 5 minutes each) with the wash buffer and a solution of horseradish peroxidase (about 1:1000 dilution, v/v) in phosphate buffered saline (PBS) containing bovine serum albumin (BSA) is subsequently applied to the strips with rocking (about 60 minutes, room temp). After the incubation time the horseradish peroxidase solution is aspirated off, the strips are washed thoroughly (3×, about 5 minutes each) with the wash buffer, and a developing solution containing 4-chloro-1-naphthol, methanol, PBS and hydrogen peroxide is added to the strips and allowed to incubate with rocking (about 30 minutes, room temp). Finally, after the development step has been completed, the solution is aspirated off and the strips are washed with wash buffer (about 5 minutes) and then reagent grade water (about 5 minutes) and allowed to dry overnight. The presence of a blue/purple color in the strips indicates the presence of anti-PVAL antibodies in the tested serum sample. The following day, the strips are mounted onto paper and the signal of unknown sera testing strips is determined by visual inspection of color intensity. Typically, a rating of negative (−), weakly positive (+/−), positive (+) or strongly positive (++) is assigned and based off of the signal intensity of the sample run as compared to the controls run in parallel (other relative intensity scales, such as 0, +1, +2, +3, +4 may, also be used as long as there are correlated controls available).

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of detecting antipolyvinyl alcohol (anti-PVAL) antibody in a human bodily fluid sample, comprising the sequential steps of:
    (a) combining the human bodily fluid sample to be tested for an anti-PVAL antibody with polyvinyl alcohol (PVAL) bound to a solid support under conditions sufficient for the formation of specific binary complex between the PVAL bound to the solid support and an anti-PVAL antibody if present in the sample;
    (b) reacting an indicator reagent that is specific for human antibodies with the binary complex to form a labeled ternary complex; wherein the indicator reagent comprises a specific binding member conjugated to a detectable label, wherein the specific binding member is specific for human antibodies;
    (c) washing away any of the sample and the indicator reagent that is not bound to the solid support; and
    d) detecting the presence or absence of the anti-PVAL antibody in the sample by detecting the presence or absence of the detectable label on the solid support.

2. The method of claim 1, wherein the solid support comprises one or more of nitrocellulose, polyvinylidene difluoride (PVDF), and nylon.

3. The method of claim 1, wherein the solid support comprises one or more of polypropylene, polystyrene, polyvinylchloride, polyamide, polycarbonate, polyether, polymethyl methacrylate, nitrocellulose, polyvinylidene difluoride, agarose, metal, and nylon.

4. The method of claim 1, wherein the solid support comprises a membrane, plastic beads, agarose beads, or magnetic beads.

5. The method of claim 1, wherein the detectable label comprises one of more of a protein, an enzyme, a radioisotope, a nucleic acid segment, a fluorochrome, and a fluorescent protein.

6. The method of claim 5, wherein the enzyme is horseradish peroxidase, alkaline phosphatase, or beta-galactosidase.

7. The method of claim 5, wherein the enzyme catalyzes the conversion of a non-chemiluminescent reagent into a chemiluminescent product.

8. The method of claim 5, wherein the enzyme catalyzes the conversion of a non-colorimetric reagent to a colorimetric product.

9. The method of claim 1, wherein the solid support is in the form of a strip and the PVAL is bound to specified regions of the strip.

10. The method of claim 1, wherein the solid support is a microtiter plate and the PVAL is bound to specified wells of the microtiter plate.

11. The method of claim 1, wherein the human bodily fluid sample comprises serum or blood.

* * * * *